US006114133A

United States Patent [19]
Seubert et al.

[11] Patent Number: 6,114,133
[45] Date of Patent: Sep. 5, 2000

[54] METHODS FOR AIDING IN THE DIAGNOSIS OF ALZHEIMER'S DISEASE BY MEASURING AMYLOID-β PEPTIDE (X-≧41)

[75] Inventors: Peter A. Seubert, South San Francisco; Carmen Vigo-Pelfrey, Mountain View; Dale B. Schenk, Pacifica; Robin Barbour, Newark, all of Calif.

[73] Assignees: Elan Pharmaceuticals, Inc., South San Francisco, Calif.; Eli Lilly & Company, Indianapolis, Ind.

[21] Appl. No.: 08/339,141

[22] Filed: Nov. 14, 1994

[51] Int. Cl.$^7$ ..................................................... G01N 33/53
[52] U.S. Cl. ........................ 435/7.94; 435/7.1; 435/7.92; 436/518; 436/811
[58] Field of Search .................................. 435/7.1, 7.92, 435/7.94, 975; 436/518, 811, 815; 530/387.9, 388.1, 387.1

[56] References Cited

U.S. PATENT DOCUMENTS

| | | |
|---|---|---|
| 4,474,892 | 10/1984 | Murad et al. . |
| 4,666,829 | 5/1987 | Glenner et al. . |
| 5,213,962 | 5/1993 | Van Nostrand et al. . |
| 5,220,013 | 6/1993 | Ponte et al. . |
| 5,223,482 | 6/1993 | Schilling, Jr., et al. . |
| 5,234,814 | 8/1993 | Card et al. . |
| 5,262,332 | 11/1993 | Selkoe . |
| 5,750,349 | 5/1998 | Suzuki et al. . |

FOREIGN PATENT DOCUMENTS

| | | |
|---|---|---|
| 0 274 826 | 7/1988 | European Pat. Off. . |
| 0-683-234 A1 | 11/1995 | European Pat. Off. . |
| 62-267297 | 11/1987 | Japan . |
| 4-252954 | 9/1992 | Japan . |
| 4-252955 | 9/1992 | Japan . |
| 4-252956 | 9/1992 | Japan . |
| WO 90/12870 | 11/1990 | WIPO . |
| WO 90/12871 | 11/1990 | WIPO . |
| WO 93/14200 | 7/1993 | WIPO . |
| WO 94/17197 | 8/1994 | WIPO . |
| WO 96/25435 | 8/1996 | WIPO . |

OTHER PUBLICATIONS

Vigo–Pelfry et al, J. Neurochemistry, 61:1965–1968, 1993.
N. Suzuki et al. (1994) *Science* 264:1336–1340. An increased Percentage of Long Amyloid β Protein Secreted by Familial Amyloid β Protein Precursor (βAPP$_{717}$) Mutants.
van Gool and Bolhuis, "Cerebrospinal Fluid Markers of Alzheimer's Disease", *JAGS*, 39:1025–1039 (1991).
Haass et al. (1992) *Nature* 359:322–325. Amyloid β–peptide is produced by cultured cells during normal metabolism.
Wolozin et al. (1987) *Annals of Neurology* 22(4):521–526. Alzheimer–Related Neuronal Protein A68: Specificity and Distribution.
Ueda et al. (1990) *The Journal of Neuroscience* 10(10):3295–3304. Alz–50 Recognizes a Phosphorylated Epitope of Tau Protein.

Chui et al. (1993) *Arch Neurol* 50:57–63. Reliability and Usefulness of a New Immunochemical Assay for Alzheimer's Disease.
H. Hamazaki (1995) *Biochem. Biophys. Res. Comm.* 211(2):349–353. Amyloid P Component Promotes Aggregation Of Alzheimer's β–Amyloid Peptide.
R. Motter et al. (1995) *Annals of Neurology* 38(4):643–648 Reduction of β–Amyloid Peptide$_{42}$ in the Cerebrospinal Fluid of Patients with Alzheimer's Disease.
L. Chang et al. (1994) *Neurology* v 44 (4 Sup. 2) β–Amyloid Protein in Cerebrospinal Fluid of Alzheimer Disease: Correlations with MMSE.
L. Higgins et al. (1994) *Annals of Neurology* 35(5):598–607 Transgenic Mouse Brain Histopathy Resembles Early Alzheimer's Disease.
G. Murphy (1994) *American J. of Pathology* 144(5):1082–1088 Development of a Monoclonal Antibody Specific for the COOH–Terminal of β–Amyloid 1–42 and Its Immunohistochemical Reactivity in Alzheimer's Disease and Related Disorders.
T. Pirttila (1994) *J. Neurological Sciences* 127:90–95. Soluble amyloid β–protein in the cerebrospinal fluid from patients with Alzheimer's disease, vascular dementia and controls.
W. Van Nostrand et al. (1992) *Proc. Natl. Acad. Sci USA* 89:2551–2555 Decreased levels of soluble amyloid β–protein precursor in cerebrospinal fluid of live Alzheimer's disease patients.
M. Tabaton et al. (1994) *Biochem. Biophys. Res. Comm.* 200(3):1598–1603 Soluble Amyloid β–Protein Is A Marker Of Alzheimer Amyloid In Brain But Not In Cerebrospinal Fluid.
C. Vigo–Pelfrey et al. (1994) *Society for Neuroscience Abstracts* vol. 20 #191.2 Detection of Aβ$_{1-42}$ In CSF And Various Cell Conditioned Media.
K. Urakami et al. (1992) *Acta Neurol Scand* 85:343–346. Amyloid βprotein precursors with kunitz–type inhibitor domains and acetyl–cholinesterase in cerebrospinal fluid from patients with dementia of the Alzheimer type.
R. Prior et al. (1991) *Neuroscience Letters* 124:69–73. Quantitative changes in the amyloid βA4 precursor protein in Alzheimer cerebrospinal fluid.
B. McDonald et al. (1988) *Alzheimer Disease and Associated Disorders* 2(3):186. The Characterisation And Purification Of A Protein Present In Cerebrospinal Fluid And Serum, Using A Monoclonal Antibody Which Reacts Immunohistochemically With Amyloid Deposits In Alzheimer Brains.

(List continued on next page.)

*Primary Examiner*—Patricia A. Duffy
*Attorney, Agent, or Firm*—Carol A. Stratford; Jean M. Duvall

[57] ABSTRACT

This invention provides methods useful in aiding in the diagnosis of Alzheimer's disease. The methods involve measuring the amount of amyloid-β peptide (x-≧41) in the cerebrospinal fluid of a patient. High levels of the peptide generally are inconsistent with a diagnosis of Alzheimer's. Low levels of the peptide are consistent with the disease and, with other tests, can provide a positive diagnosis.

20 Claims, 2 Drawing Sheets

OTHER PUBLICATIONS

D. Allsop (1986) *Neuroscience Letters* 68:252–256. Monoclonal Antibodies Raised Against A Subsequence Of Senile Plaque Core Protein React With Plaque Cores. Plaque Periphery And Cerebrovascular Amyloid In Alzheimer's Disease.
T. Ishii (1986) *Neuropathology and Applied Neurobiology* 12:441–445. A Monoclonal Antibody To Amyloid In The Brains Of Patients With Alzheimer's Disease.
Glenner and Wong (1984) Biochem. Biophys. Res. Commun. 120:885–890.
Kang et al. (1987) Nature 325:733–736.
Roher et al. (1993) Proc. Natl. Acad. Sci. USA 90:1086–840.
Iwatsubo et al. (1994) Neuron 13:45–53.
Selkoe (1994) J. Neuropath. and Exp. Neurol. 53:438–447.
Selkoe (1991) Neuron 6:487.
Goate et al. (1991) Nature 349:704–706.
Chartier Harlan et al. (1991) Nature 353:844–846.
Murrell et al. (1991) Science 254:97–99.
Suzuki et al. (1994) Science 264:1336–1340.
Mullan et al. (1992) Nature Genet 1:345–347.
Glenner and Wong (1984) Biochem. Biophys. Res. Commun. 122:1131–1135.
Masters et al. (1985) Proc. Natl. Acad. Sci. USA 82:4245–4249.
Selkoe et al. (1986) J. Neurochem. 46:1820–1834.
Joachim et al. (1988) Brain Research 474:100–111.
Hilbich et al. (1991) J. Mol. Biol. 218:149–163.
Barrow and Zagorski (1991) Science 253:179–182.
Burdick et al. (1992) J. Biol. Chem. 267:546–554.
Palmert et al. (1989) Proc. Natl. Acad. Sci. USA 86:6338–6342.
Weidemann et al. (1989) Cell 57:115–126.
Henriksson et al. (1991) J. Neurochem. 56:1037–1042.
Palmert et al. (1990) Neurology 40:1028–1034.
Seubert et al. (1993) Nature 361:260–263.
Podlisny et al. (1990) Biochem. Biophys. Res. Commun. 167:1094–1101.
Rumble et al. (1989) N. Engl. J. Med. 320:1446–1452.
Schlossmacher et al. (1992) Neurobiol. Aging 13:421–434.
Wong et al. (1984) Proc. Natl. Acad. Sci USA 82:8729–8732.
Selkoe (1986) Neurobiol. Aging 7:425–432.
Pardridge et al. (1987) Biochem. Biophys. Res. Commun. 145:241–248.
Joachim et al. (1989) Nature 341:226–230.
Selkoe et al. (1989) Neurobiol. Aging 10:387–395.
Wisniewski, Alzheimer's disease, eds. Becker and Giocobini, Taylor and Francas, N.Y. p. 206, 1990.
Kim and Wisniewski, Techniques in Diagnostic Pathology, eds, Bullock et al., Academic Press, Boston p. 106.
Seubert et al. (1992) Nature 359:325–327.
Vigo–Pelfrey et al. (1993) J. Neurochem. 61:1965–1968.
Esch et al. (1990) Science 248:1122.
Anderson et al. (1991) Neuro Science Lett. 128:126–128.
Ponte et al. (1988) Nature 331:525–527.
Tanzi et al. (1988) Nature 331:528–530.
Kitaguchi et al. (1988) Nature 331:530–532.
Hardy (1992) Nature Genet. 1:233–234.

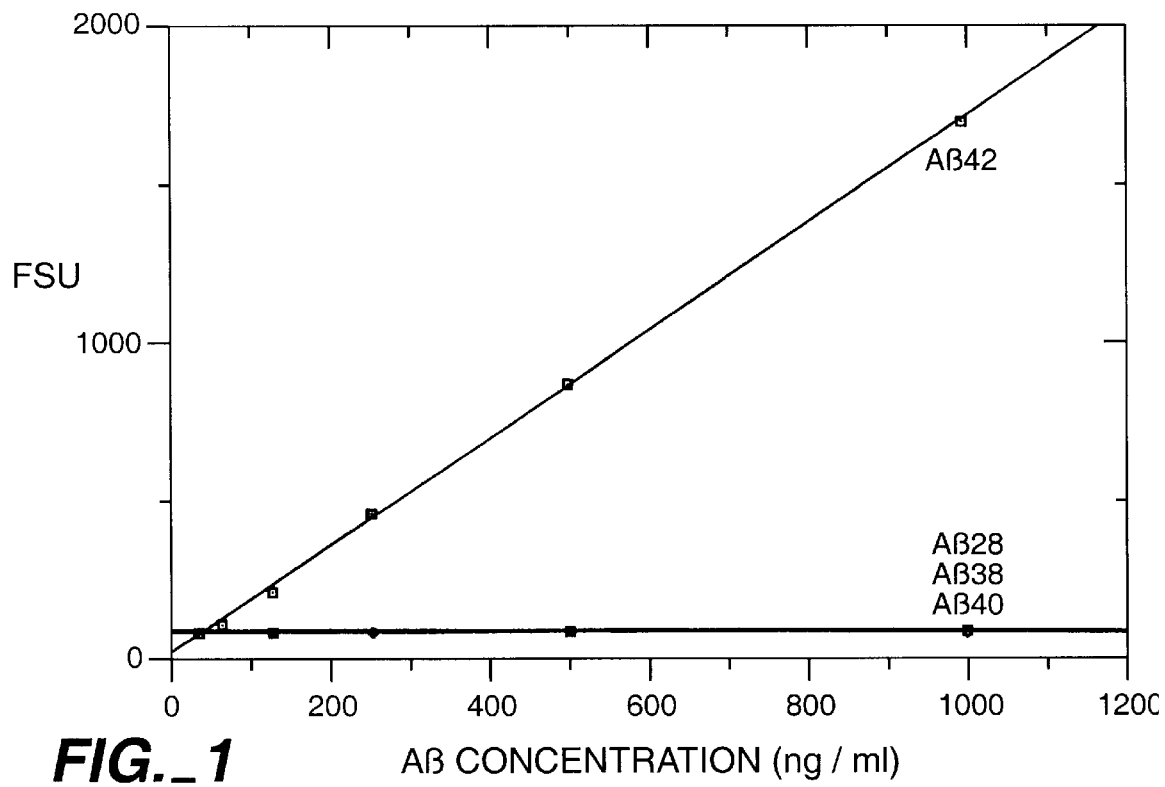
FIG._1
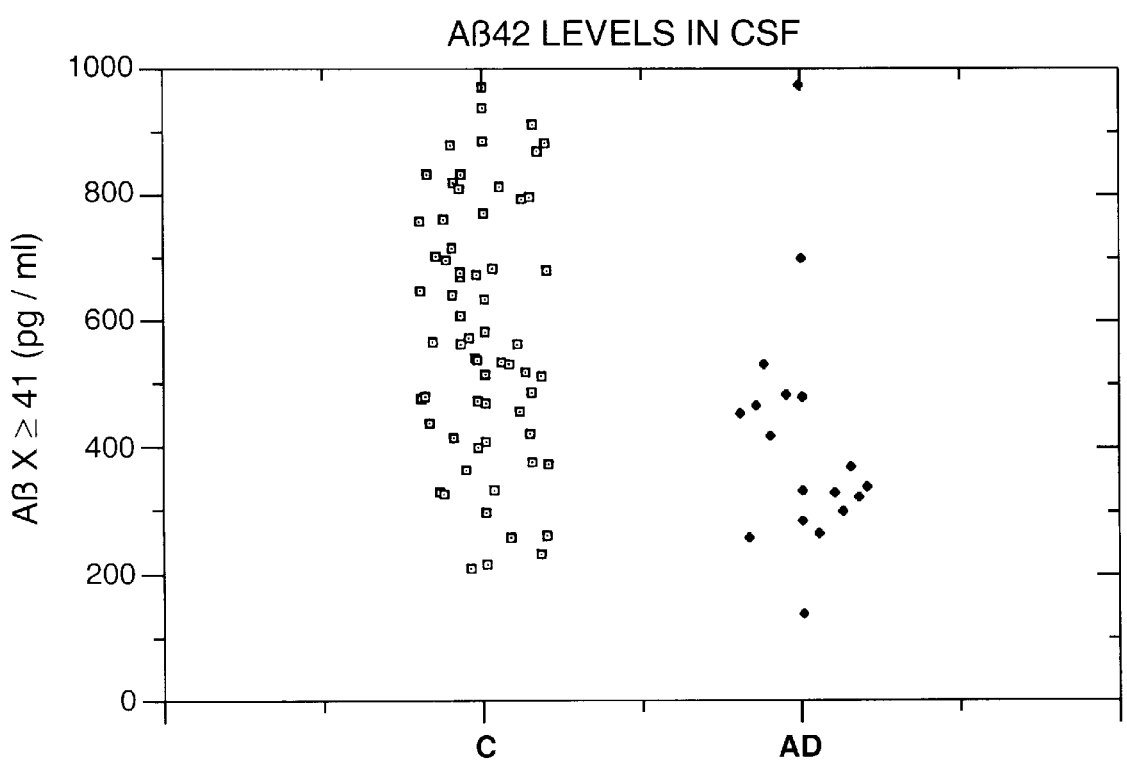
FIG._2

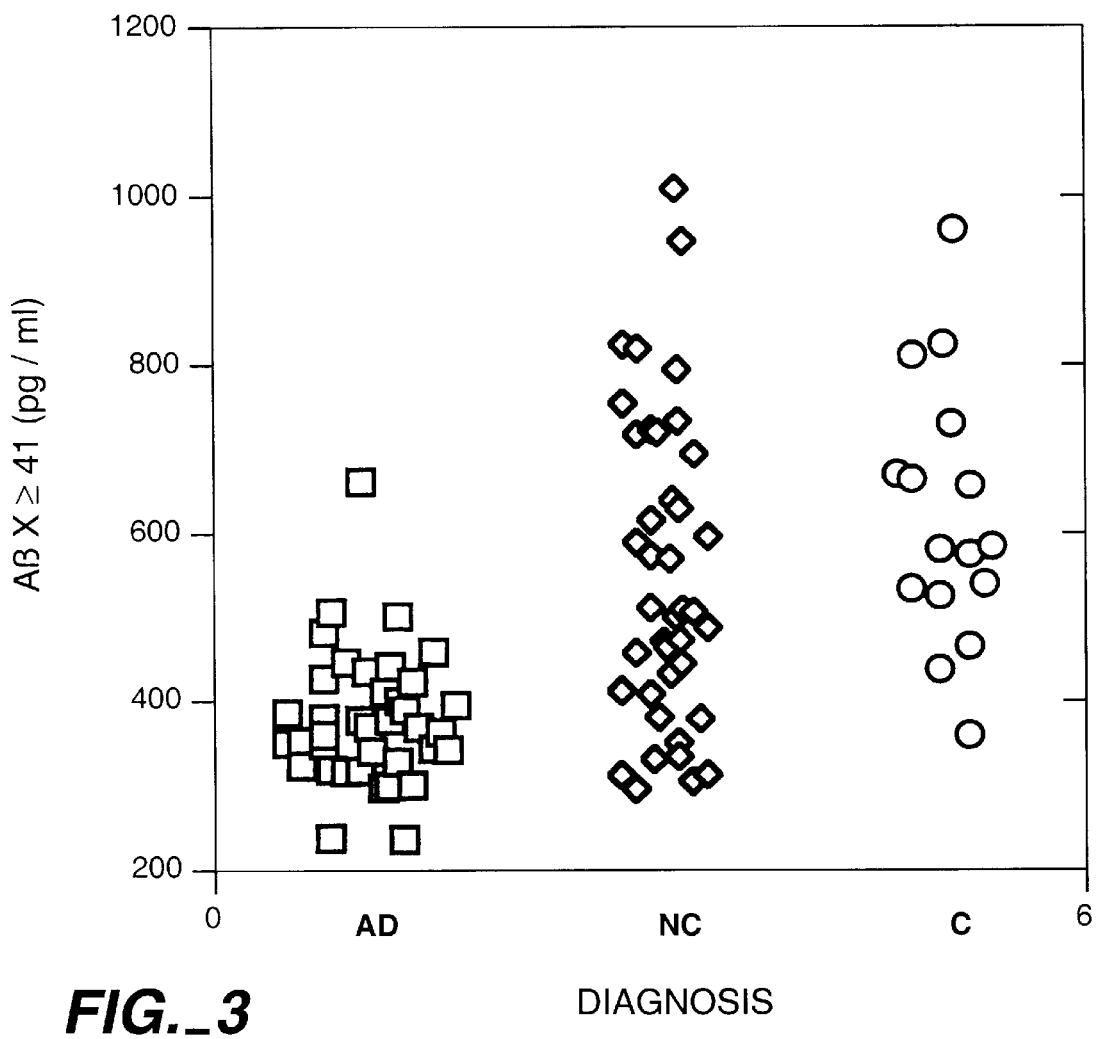
FIG._3

METHODS FOR AIDING IN THE DIAGNOSIS OF ALZHEIMER'S DISEASE BY MEASURING AMYLOID-β PEPTIDE (X-≧41)

This application is related to application Ser. No. 07/965,972, filed Oct. 26, 1992 now abandoned and Ser. No. 08/079,511, filed Jun. 17, 1993 now U.S. Pat. No. 5,766,846, both incorporated herein by reference.

BACKGROUND OF THE INVENTION

1. Field of the Invention

The present invention relates generally to methods for diagnosing or monitoring Alzheimer's disease. More particularly, the present invention relates to measuring the amount of β amyloid peptide (x-≧41) in patient fluid samples and using this amount as a diagnostic indicator.

Alzheimer's disease (AD) is a degenerative brain disorder characterized clinically by progressive loss of memory, cognition, reasoning, judgment and emotional stability that gradually leads to profound mental deterioration and ultimately death. AD is a very common cause of progressive mental failure (dementia) in aged humans and is believed to represent the fourth most common medical cause of death in the United States. AD has been observed in all races and ethnic groups worldwide and presents a major present and future public health problem. The disease is currently estimated to affect about two to three million individuals in the United States alone. AD is at present incurable. No treatment that effectively prevents AD or reverses its symptoms or course is currently known.

The brains of individuals with AD exhibit characteristic lesions termed senile plaques, and neurofibrillary tangles. Large numbers of these lesions are generally found in several areas of the human brain important for memory and cognitive function in patients with AD. Smaller numbers of these lesions in a more restricted anatomical distribution are sometimes found in the brains of aged humans who do not have clinical AD. Senile plaques and amyloid angiopathy also characterize the brains of individuals beyond a certain age with Trisomy 21 (Down's Syndrome) and Hereditary Cerebral Hemorrhage with Amyloidosis of the Dutch-Type (HCHWA-D). At present, a definitive diagnosis of AD usually requires observing the aforementioned lesions in the brain tissue of patients who have died with the disease or, rarely, in small biopsied samples of brain tissue taken during an invasive neurosurgical procedure.

The principal chemical constituent of the senile plaques and vascular amyloid deposits (amyloid angiopathy) characteristic of AD and the other disorders mentioned above is an approximately 4.2 kilodalton (kD) protein of about 39–43 amino acids designated the amyloid-β peptide (Aβ) or sometimes βAP, AβP or β/A4. Aβ was first purified and a partial amino acid sequence reported in Glenner and Wong (1984) Biochem. Biophys. Res. Commun. 120:885–890. The isolation procedure and the sequence data for the first 28 amino acids are described in U.S. Pat. No. 4,666,829. Forms of Aβ having amino acids beyond number 40 were first reported by Kang et al. (1987) Nature 325:733–736.

Roher et al. (1993) Proc. Natl. Acad. Sci. USA 90:10836–840 showed that Aβ(1–42) is the major constituent in neuritic plaques (90%) with significant amounts of isomerized and racemized aspartyl residues. The authors also showed that Aβ(17–42) also predominates in diffuse plaques (70%), while Aβ(1–40) is the major constituent in the meningovascular plaques, comprising 60% of the total Aβ and, in parenchymal vessel deposits Aβ(1–42) represents 75% of the total Aβ. Iwatsubo et al. (1994) Neuron 13:45–53 showed that Aβ42(43)-positive senile plaques are the major species in sporadic Aβ brain.

Molecular biological and protein chemical analyses conducted during the last several years have shown that Aβ is a small fragment of a much larger precursor protein, referred to as the β-amyloid precursor protein (APP), that is normally produced by cells in many tissues of various animals, including humans. Knowledge of the structure of the gene encoding APP has demonstrated that Aβ arises as a peptide fragment that is cleaved from the carboxy-terminal end of APP by as-yet-unknown enzymes (proteases). The precise biochemical mechanism by which the Aβ fragment is cleaved from APP and subsequently deposited as amyloid plaques in the cerebral tissue and in the walls of cerebral and meningeal blood vessels is currently unknown.

Several lines of evidence indicate that progressive cerebral deposition of Aβ plays a seminal role in the pathogenesis of Aβ and can precede cognitive symptoms by years or decades (for review, see Selkoe (1994) J. Neuropath. and Exp. Neurol. 53:438–447 and Selkoe (1991) Neuron 6:487). The single most important line of evidence is the discovery in 1991 that missense DNA mutations at amino acid 717 of the 770-amino acid isoform of APP can be found in affected members but not unaffected members of several families with a genetically determined (familial) form of AD (Goate et al. (1991) Nature 349:704–706; Chartier Harlan et al. (1991) Nature 353:844–846; and Murrell et al. (1991) Science 254:97–99). Suzuki et al. (1994) Science 264:1336–1340 showed that in persons with the 717 mutation, there is a higher percentage of Aβ(1–42) than Aβ(1–40).

In addition, a double mutation changing lysine$^{595}$-methionine$^{595}$ to asparagine$^{595}$-leucine$^{596}$ (with reference to the 695 isoform) found in a Swedish family was reported in 1992 (Mullan et al. (1992) Nature Genet 1:345–347) and is referred to as the Swedish variant. Genetic linkage analyses have demonstrated that these mutations, as well as certain other mutations in the APP gene, are the specific molecular cause of AD in the affected members of such families. In addition, a mutation at amino acid 693 of the 770-amino acid isoform of APP has been identified as the cause of the Aβ deposition disease, HCHWA-D, and a change from alanine to glycine at amino acid 692 appears to cause a phenotype that resembles AD in some patients but HCHWA-D in others. The discovery of these and other mutations in APP in genetically based cases of AD argues that alteration of APP and subsequent deposition of its Aβ fragment can cause AD.

Despite the progress which has been made in understanding the underlying mechanisms of AD, there remains a need to develop methods for use in diagnosis of the disease. It would be further desirable to provide methods for use in diagnosis of Aβ-related conditions, where the diagnosis is based at least in part on detection of Aβ and related fragments in patient fluid samples. Specific assays for Aβ detection should be capable of detecting Aβ and related fragments in fluid samples at very low concentrations as well as distinguishing between Aβ and other fragments of APP which may be present in the sample.

2. Description of the Background Art

Glenner and Wong (1984) Biochem. Biophys. Res. Commun. 120:885–890 and U.S. Pat. No. 4,666,829, are discussed above. The '829 patent suggests the use of an antibody to the 28 amino acid Aβ fragment to detect "Alzheimer's Amyloid Polypeptide" in a patient sample and diagnose AD. No data demonstrating detection or diagnosis are presented.

Numerous biochemical electron microscopic and immunochemical studies have reported that Aβ is highly insoluble in physiologic solutions at normal pH. See, for example, Glenner and Wong (1984) Biochem. Biophys. Res. Commun. 122:1131–1135; Masters et al. (1985) Proc. Natl. Acad. Sci. USA 82:4245–4249; Selkoe et al. (1986) J. Neurochem. 46:1820–1834; Joachim et al. (1988) Brain Research 474:100–111; Hilbich et al. (1991) J. Mol. Biol. 218:149–163; Barrow and Zagorski (1991) Science 253:179–182; and Burdick et al. (1992) J. Biol. Chem. 267:546–554. Furthermore, this insolubility was predicted by and is consistent with the amino acid sequence of Aβ which includes a stretch of hydrophobic amino acids that constitutes part of the region that anchors the parent protein (APP) in the lipid membranes of cells. Hydrophobic, lipid-anchoring proteins such as Aβ are predicted to remain associated with cellular membranes or membrane fragments and thus not be present in physiologic extracellular fluids. The aforementioned studies and many others have reported the insolubility in physiologic solution of native Aβ purified from AD brain amyloid deposits or of synthetic peptides containing the Aβ sequence. The extraction of Aβ from cerebral amyloid -deposits and its subsequent solubilization has required the use of strong, non-physiologic solvents and denaturants. Physiologic, buffered salt solutions that mimic the extracellular fluids of human tissues have uniformly failed to solubilize Aβ.

Separate attempts to detect APP or fragments thereof in plasma or CSF have also been undertaken. A large secreted fragment of APP that does not contain the intact Aβ region has been found in human cerebrospinal fluid (Palmert et al. (1989) Proc. Natl. Acad. Sci. USA 86:6338–6342; Weidemann et al. (1989) Cell 57:115–126; Henriksson et al. (1991) J. Neurochem. 56:1037–1042; Palmert et al. (1990) Neurology 40:1028–1034; and Seubert et al. (1993) Nature 361:260–263) and in plasma (Podlisny et al. (1990) Biochem. Biophys. Res. Commun. 167:1094–1101). The detection of fragments of the carboxy-terminal portion of APP in plasma has also been reported (Rumble et al. (1989) N. Engl. J. Med. 320:1446–1452), as has the failure to detect such fragments (Schlossmacher et al. (1992) Neurobiol. Aging 13:421–434).

Despite the apparent insolubility of native and synthetic Aβ, it had been speculated that Aβ might occur in body fluids, such as cerebrospinal fluid (CSF) or plasma (Wong et al. (1984) Proc. Natl. Acad. Sci. USA 92:8729–8732; Selkoe (1986) Neurobiol. Aging 7:425–432; Pardridge et al. (1987) Biochem. Biophys. Res. Commun. 145:241–248; Joachim et al. (1989) Nature 341:226–230; Selkoe et al. (1989) Neurobiol. Aging 10:387–395).

Several attempts to measure Aβ in CSF and plasma have been reported by both radioimmunoassay methods (WO90/12870 published Nov. 1, 1990) and sandwich ELISAs (Wisniewski in *Alzheimer's disease*, eds. Becker and Giacobini, Taylor and Francas, N.Y. pg. 206, 1990; Kim and Wisniewski in *Techniques in Diagnostic Pathology*, eds. Bullock et al., Academic Press, Boston pg. 106; and WO90/12871 published Nov. 1, 1990). While these reports detected very low levels of Aβ immunoreactivity in bodily fluids, attempts to directly purify and characterize this immunoreactivity further and determine whether it represented Aβ were not pursued, and the efforts were abandoned. The possibility of Aβ production by cultured cells was neither considered nor demonstrated.

Retrospectively, the inability to readily detect Aβ in bodily fluids was likely due to the presence of amyloid precursor fragments with overlapping regions or fragments of Aβ that obscured measurements and to the lack of antibodies completely specific for intact Aβ. This is presumably because the antibodies used by both groups would cross-react with other APP fragments containing part of Aβ known to be present in CSF thereby interfering with the measurement, if any, of intact Aβ. These difficulties have been overcome with the use of monoclonal antibodies specific to an epitope in the central junction region of intact Aβ(Seubert et al. (1992) Nature 359:325–327).

Seubert et al. (1992) Nature 359:325–327 and Shoji et al. Science (1992) 258:126–129 provided the first biochemical evidence for the presence of discrete Aβ in bodily fluids. Vigo-Pelfrey et al. (1993) J. Neurochem. 61:1965–1968 reported the identification of many Aβ species in cerebrospinal fluid.

SUMMARY OF THE INVENTION

The present invention provides methods useful for aiding in the diagnosis and monitoring of Aβ-related conditions in patients, where the methods rely on the specific detection in patient fluid samples of one or more soluble Aβ or soluble Aβ fragments having amino acid residues beyond number 40 in their carboxy-terminal end. These peptides are designated "Aβ(x-≧41)" (Aβ from amino acid number "x" to an amino acid greater than or equal to amino acid number 41). In one embodiment, the measured peptides belong to the class of Aβ(x-≧41) that contain at least amino acids 13–41.

For the diagnosis and monitoring of Aβ-related conditions, the amount of the aforementioned peptides in a patient fluid sample, especially cerebrospinal fluid (CSF), is measured and compared with a predetermined value, such as an indicator value (in the case of diagnosis) or a prior patient value (in the case of monitoring). In the case of diagnosis, measured amounts of Aβ(x-≧41) which are above the indicator value are considered to be a strong indication that the patient is not suffering from Aβ or other Aβ-related condition. However, this information may also be considered together with other factors in making a determinative diagnosis. Measured amounts of Aβ(x-≧41) which are at or below the indicator value are considered to be a positive indication that the patient may be suffering from AD or other Aβ-related condition. The low Aβ(x-≧41) status of the tested individual will usually not by itself be considered a determinative diagnostic of an Aβ-related condition, but instead will be considered together with other accepted clinical symptoms of Aβ-related conditions in making a diagnosis. In cerebrospinal fluid, an indicator value of about 0.5 ng/ml is useful.

In a particular aspect, the present invention provides specific binding assays which are useful for detecting soluble Aβ(x-≧41) in fluid samples and which may be employed in patient diagnostic and monitoring methods just described. Specific binding assays according to the present invention employ two binding substances specific for different epitopes or determinant sites on the Aβ(x-≧41) molecule. One epitope or site is generally not found on other fragments or degradation products of the amyloid-β precursor protein (APP), so as to avoid cross-reaction with those fragments. Particularly useful are antibodies which recognize a junction region within Aβ, where the junction region is located about the site of normal proteolytic cleavage of APP between residues Lys[16] and Leu[17] (Esch et al. (1990) Science 248:492–495 and Anderson et al. (1991) Neuro. Science Lett. 128:126–128), typically spanning amino acid residues 13 to 26. The other epitope or site contains at least one amino acid beyond amino acid number 40 of Aβ that is essential for recognition, but does not cross-react with Aβ or Aβ fragments whose carboxy-terminal amino acid is number 40 or less. Exemplary specific binding assays include two-site (sandwich) assays in which the capture antibody is specific for the junction region of Aβ, as just described, and a second detectable antibody is specific for an epitope or site containing at least one Aβ amino acid beyond number 40. In particular, the second antibody can be produced by immunization with a hapten containing Aβ amino acids 33–42.

In another aspect, the present invention provides a system for detecting one or more soluble Aβ(x-≧41) in a fluid sample. The system includes a first binding substance, typically an antibody, specific for an epitope in a junction region of Aβ, as described above, and a second binding substance, typically an antibody, specific for an epitope of Aβ containing an amino acid beyond amino acid number 40 of Aβ at the carboxy-terminus essential for recognition. The first binding substance is an anti-Aβ antibody bound to a solid phase, while the other is a reporter antibody against the Aβ carboxy-terminus. The reporter antibody can, itself, be labeled, or can be detectable by another antibody (e.g., a rabbit antibody recognizable by labeled or enzyme-conjugated anti-rabbit antibodies.) The system can further include substrate for an enzyme label. The system is useful in performing enzyme-linked immunosorbent assays (ELISA) having high specificity and sensitivity for the detection of Aβ(x-≧41) in fluid samples.

In another aspect, this invention provides methods for screening a compound to determine its ability to alter the amount of Aβ(x-≧41) in the CSF. The methods involve measuring a first amount of soluble Aβ(x-≧41) in the CSF of a non-human animal used as a model of Alzheimer's disease; administering the compound to the non-human animal; measuring a second amount of soluble Aβ(x-≧41) in the CSF of the non-human animal; and comparing the first amount with the second amount. The difference indicates whether the compound increases Aβ(x-≧41) in the CSF, in which case it might be useful in the treatment of Alzheimer's; or decreases the amount, in which case the compound might aggravate hasten Alzheimer's. The non-human animal preferably is a mouse or a hamster.

BRIEF DESCRIPTION OF THE DRAWINGS

FIG. 1 shows the results of ELISA assays using antibody 266 (directed to the Aβ junction region) and antibody 277/2 (directed to Aβ amino acids 33–42) to detect Aβ(42), but not Aβ(28), Aβ(38), or Aβ(40).

FIG. 2 shows the amounts of Aβ(x-≧41) in CSF of control patients (C) and AD patients (AD) in Group A as detected by ELISA.

FIG. 3 shows the amounts of Aβ(x-≧41) in CSF of AD patients (AD), non-Alzheimer's neurological controls (NC) and controls (C) in Group B as detected by ELISA.

DESCRIPTION OF THE SPECIFIC EMBODIMENTS

The present invention results at least in part from the discovery that the cerebrospinal fluid ("CSF") of individuals suffering from Alzheimer's disease generally contains Aβ(x-≧41) in amounts which are in the very low end of the normal range present in the CSF of non-Alzheimer's individuals and, in particular, below about 0.5 ng/ml. This discovery is surprising because the bulk of Aβ deposits in the brain tissue of persons suffering from Alzheimer's disease is Aβ(1–42), and is significantly elevated compared to the amount of Aβ(1–42) in non-Alzheimer's individuals.

Based on this discovery, the present invention provides methods for diagnosing and monitoring Alzheimer's disease. According to the methods, a patient sample is first obtained. The patient sample is usually a fluid sample and, preferably, cerebrospinal fluid. Then the amount of soluble Aβ(x-≧41) in the patient sample is measured. A preferred method of measuring the amount is by using the sandwich assay described herein. The measured amount is then compared with a predetermined value, such as an indicator value in the case of diagnosis, or a prior patient value in the case of monitoring. The status of the patient is assessed based on the difference between the two amounts.

As described in more detail below, the methods of the present invention will be useful as both a positive and negative indicator of AD and other Aβ-related conditions in tested individuals. The data in the Experimental section show that individuals not suffering from Alzheimer's disease have CSF concentrations of soluble Aβ(x-≧41) that range from about 0.2 ng/ml to about 1.0 ng/ml. However, patients with Alzheimer's disease have CSF concentrations of soluble Aβ(x-≧41) generally below 0.5 ng/ml. Therefore, a measured amount above the indicator value of about 0.5 ng/ml is a very strong negative indication of Alzheimer's disease. That is, individuals having such levels are considered to be less likely to suffer from Aβ-related condition. An indicator value of 0.7 ng/ml will reduce the number of false negatives detected and is also useful as a predetermined amount. By contrast, a measured amount below the indicator value of 0.5 ng/ml is a positive indicator of Alzheimer's disease and individuals having these levels are considered to be more likely to suffer from Alzheimer's disease. An indicator value of 0.45 ng/ml reduces the number of false positives and is also useful as a predetermined value. However, since values below 0.5 ng/ml and 0.45 ng/ml are at the low end of the normal range found in non-Alzheimer individuals, a measured amount below the indicator level does not, by itself, suffice to provide a diagnosis of Alzheimer's disease. Therefore, the methods of the present invention will be useful as part of a diagnosis procedure which will also consider other known AD symptoms, such as those described in the NIHCDS-ADRDA criteria (e.g., clinical dementia and memory impairment).

The sandwich assay described in the Experimental section used antibodies raised against the junction region of Aβ and against residues 33–42 of Aβ. In this assay, Alzheimer's patients generally had levels of Aβ(x-≧41) below 0.5 ng/ml as detected by the antibodies. The indicator value of 0.5 ng/ml is, in part, a function of the particular peptides recognized by the antibodies used as well as the peptide lot used in making the calibration. Therefore, the practitioner may base the predetermined amount on a re-calibration using reagents and protocols to be used in measuring Aβ(x-≧41) in the test.

In addition to initial diagnosis of the Aβ-related condition, the measured concentrations of Aβ may be monitored in order to follow the progress of the disease, and potentially follow the effectiveness of treatment (when such treatments become available). It would be expected that levels of Aβ(x-≧41) would decrease as the disease progressed.

The term "amyloid-β peptide," or "Aβ" as used herein refers to an approximately 4.2 kD protein which, in the brains of AD, Down's Syndrome, HCHWA-D and some normal aged subjects, forms the subunit of the amyloid filaments comprising the senile (amyloid) plaques and the amyloid deposits in small cerebral and meningeal blood vessels (amyloid angiopathy). Aβ can occur in a filamentous polymeric form (in this form, it exhibits the Congo-red and thioflavin-S dye-binding characteristics of amyloid described in connection therewith). Aβ can also occur in a non-filamentous form ("preamyloid" or "amorphous" or "diffuse" deposits) in tissue, in which form no detectable birefringent staining by Congo red occurs. A portion of this protein in the insoluble form obtained from meningeal blood vessels is described in U.S. Patent No. 4,666,829. Aβ is an approximately 39–43 amino acid fragment of a large membrane-spanning glycoprotein, referred to as the β-amyloid precursor protein (APP), encoded by a gene on the long arm of human chromosome 21. Forms of Aβ longer than 43 amino acids are also contemplated herein. Aβ is further characterized by its relative mobility in SDS-polyacrylamide gel electrophoresis or in high performance liquid chromatography (HPLC). A sequence for a 43-amino acid-version of Aβ is:

1
Asp Ala Glu Phe Arg His Asp Ser Gly Tyr
11
Glu Val His His Gln Lys Leu Val Phe Phe
21
Ala Glu Asp Val Gly Ser Asn Lys Gly Ala
31
Ile Ile Gly Leu Met Val Gly Gly Val Val
41
Ile Ala Thr [SEQ ID NO:1].

As used herein, Aβ also refers to related polymorphic forms of Aβ, including those that result from mutations in the Aβ region of the APP normal gene.

The term "Aβ fragment" as used herein refers to fragments and degradation products of Aβ which are generated at low concentrations by mammalian cells. Particular Aβ fragments have a molecular weight of approximately 3 kD and are presently believed to include peptides with, for example, amino acid residues 3–34, 6–27, 6–34, 6–35, 6–42, 11–34, 11–40, 17–40, 11–43 and 12–43 of Aβ.

As used herein, the term "Aβ(x-≧41)" refers to Aβ whose amino-terminus begins at amino acid number 1 of Aβ or which is truncated, and whose carboxy-terminus extends beyond amino acid number 40. These peptides and fragments comprise a heterogenous group. For example, Aβ(6–42), Aβ(11–43) and Aβ(12–43) all have been found in the CSF. However, this list is not meant to be exclusive. Other peptides from among the group are presumed to exist in the CSF and are detectable with the methods described herein.

The particular peptides measured from among the group of all Aβ(x-≧41) depends on the particular measuring method used. In the case of using binding substances, such as antibodies, the binding substance can be directed to one or more from among the group of peptides. For example, an antibody raised against amino acids 33–42 of Aβ that does not cross react with Aβ(1–40) will bind to Aβ(x-42). It also may bind to Aβ(x-41) and Aβ(x-43). According to one embodiment of the invention, the method involves determining the amount of Aβ(x-≧41) having at least amino acids 13–41 of Aβ. These species can be measured using a sandwich assay employing antibodies that recognize the junction region (amino acids 13–26) and antibodies produced by immunization with a hapten having Aβ amino acids 33–42, as described in the Example.

The term "Aβ junction region" as used herein refers to a region of Aβ which is centered at the site between amino acid residues 16 and 17 (Lys$^{16}$ and Leu$^{17}$) which is a target for proteolytic processing of APP. Such processing results in a variety of APP fragments which may, for example, terminate at amino acid 16 of Aβ and which, therefore, are potentially immunologically cross-reactive with antibodies to the intact Aβ molecule which are to be identified in the methods of the present invention. Antibodies raised against a synthetic peptide consisting of amino acid residues 13–26 having been found to display the requisite specificity.

The term "amyloid-β precursor protein" (APP) as used herein is defined as a polypeptide that is encoded by a gene of the same name localized in humans on the long arm of chromosome 21 and that includes Aβ within its carboxyl third. APP is a glycosylated, single-membrane-spanning protein expressed in a wide variety of cells in many mammalian tissues. Examples of specific isotypes of APP which are currently known to exist in humans are the 695-amino acid polypeptide described by Kang et al. (1987) Nature 325:733–736 which is designated as the "normal" APP; the 751-amino acid polypeptide described by Ponte et al. (1988) Nature 331:525–527 (1988) and Tanzi et al. (1988) Nature 331:528–530; and the 770-amino acid polypeptide described by Kitaguchi et al. (1988) Nature 331:530–532. Examples of specific variants of APP include point mutations which can differ in both position and phenotype (for review of known variant mutations see Hardy (1992) Nature Genet. 1:233–234).

The term "Aβ-related condition" as used herein is defined as including Alzheimer's disease (which includes familial Alzheimer's disease), Down's Syndrome, HCHWA-D, and advanced aging of the brain.

The term "body fluid" as used herein refers to those fluids of a mammalian host which will be expected to contain measurable amounts of Aβ and Aβ fragments, specifically including cerebrospinal fluid (CSF), blood, urine, and peritoneal fluid. The term "blood" refers to whole blood, as well as blood plasma and serum.

The methods and systems of this invention involve the ability to detect species of Aβ extending beyond amino acid number 40 at the carboxy-terminal end and, therefore, to distinguish them from shorter species, such as Aβ(40). While detection of Aβ(x-≧41) can be accomplished by any methods known in the art for detecting peptides, the use of immunological detection techniques employing binding substances such as antibodies, antibody fragments, recombinant antibodies, and the like, is preferred. Particularly suitable detection techniques include ELISA, Western blotting, radioimmunoassay, and the like. Suitable immunological methods employing a single antibody are also contemplated, for example, radioimmunoassay using an antibody specific for 241 forms of Aβ, or single antibody ELISA methods.

Thus, this invention also provides antibodies specific for Aβ(x-≧41) that do not cross react with Aβ(≧40). These antibodies can be made by immunizing animals with synthetic peptides that include amino acids beyond number 40 of Aβ. For example, the synthetic peptide can include amino acids 33–42. A specific example of the production of such an antibody is provided in the Experimental section.

According to one embodiment of the invention, detection and measurement of Aβ(x-≧41) peptides involves the use of two antibodies, one specific for an epitope containing amino acids beyond number 40 in Aβ, and another antibody capable of distinguishing Aβ and Aβ fragments from other APP fragments which might be found in the sample. In particular, it has been found that antibodies which are monospecific for the junction region of Aβ are capable of distinguishing Aβ from other APP fragments. The junction region of Aβ is centered at amino acid residues 16 and 17, typically spanning amino acid residues 13–26, and such junction-specific antibodies may be prepared using synthetic peptides having that sequence as an immunogen.

A preferred immunoassay technique is a two-site or "sandwich" assay employing a junction-specific antibody as the capture antibody (bound to a solid phase) and a second antibody which binds to an epitope containing amino acids beyond number 40 in Aβ. Particular methods for preparing such antibodies and utilizing such antibodies in an exemplary ELISA are set forth in the Experimental section hereinafter and in related U.S. Pat. No. 5,593,846, supra.

Antibodies specific for Aβ may be prepared against a suitable antigen or hapten comprising the desired target epitope, such as the junction region consisting of amino acid residues 13–26 and the carboxy terminus consisting of amino acid residues 33–42. Conveniently, synthetic peptides may be prepared by conventional solid phase techniques, coupled to a suitable immunogen, and used to prepare antisera or monoclonal antibodies by conventional techniques. Suitable peptide haptens will usually comprise at least five contiguous residues within Aβ and may include more than six residues.

Synthetic polypeptide haptens may be produced by the well-known Merrifield solid-phase synthesis technique in which amino acids are sequentially added to a growing chain (Merrifield (1963) J. Am. Chem. Soc. 85:2149–2156). The amino acid sequences may be based on the sequence of Aβ set forth above.

Once a sufficient quantity of polypeptide hapten has been obtained, it may be conjugated to a suitable immunogenic carrier, such as serum albumin, keyhole limpet hemocyanin, or other suitable protein carriers, as generally described in Hudson and Hay, *Practical Immunology*, Blackwell Scientific Publications, Oxford, Chapter 1.3, 1980, the disclosure of which is incorporated herein by reference. An exemplary immunogenic carrier utilized in the examples provided below is α-CD3ε antibody (Boehringer-Mannheim, Clone No. 145-2C11).

Once a sufficient quantity of the immunogen has been obtained, antibodies specific for the desired epitope may be produced by in vitro or in vivo techniques. In vitro techniques involve exposure of lymphocytes to the immunogens, while in vivo techniques require the injection of the immunogens into a suitable vertebrate host. Suitable vertebrate hosts are non-human, including mice, rats, rabbits, sheep, goats, and the like. Immunogens are injected into the animal according to a predetermined schedule, and the animals are periodically bled, with successive bleeds having improved titer and specificity. The injections may be made intramuscularly, intraperitoneally, subcutaneously, or the like, and an adjuvant, such as incomplete Freund's adjuvant, may be employed.

If desired, monoclonal antibodies can be obtained by preparing immortalized cell lines capable of producing antibodies having desired specificity. Such immortalized cell lines may be produced in a variety of ways. Conveniently, a small vertebrate, such as a mouse, is hyperimmunized with the desired immunogen by the method just described. The vertebrate is then killed, usually several days after the final immunization, the spleen cells removed, and the spleen cells immortalized. The manner of immortalization is not critical. Presently, the most common technique is fusion with a myeloma cell fusion partner, as first described by Kohler and Milstein (1975) Nature 256:495–497. Other techniques including EBV transformation, transformation with bare DNA, e.g., oncogenes, retroviruses, etc., or any other method which provides for stable maintenance of the cell line and production of monoclonal antibodies. Specific techniques for preparing monoclonal antibodies are described in *Antibodies: A Laboratory Manual*, Harlow and Lane, eds., Cold Spring Harbor Laboratory, 1988, the full disclosure of which is incorporated herein by reference.

In addition to monoclonal antibodies and polyclonal antibodies (antisera), the detection techniques of the present invention will also be able to use antibody fragments, such as F(ab), Fv, $V_L$, $V_H$, and other fragments. In the use of polyclonal antibodies, however, it may be necessary to adsorb the anti-sera against the target epitopes in order to produce a monospecific antibody population. It will also be possible to employ recombinantly produced antibodies (immunoglobulins) and variations thereof as now well described in the patent and scientific literature. See, for example, EPO 8430268.0; EPO 85102665.8; EPO 85305604.2; PCT/GB 85/00392; EPO 85115311.4; PCT/US86/002269; and Japanese application 85239543, the disclosures of which are incorporated herein by reference. It would also be possible to prepare other recombinant proteins which would mimic the binding specificity of antibodies prepared as just described.

Animal models are currently being used to study Alzheimer's disease. (See, e.g., International Patent Application WO 93/14200 and U.S. Pat. No. 5,604,102, both incorporated herein by reference.) These models are useful for screening compounds for their ability to effect the course of Alzheimer's disease, both to ameliorate and aggravate the condition. Since AD is characterized by a decrease in the amounts of Aβ(x-≧41) in the CSF, it is expected that effective treatments for Alzheimer's disease will result in an increase in amount of Aβ(x-≧41) in the CSF, while agents that hasten progress of the disease will result in a decrease in the amount of Aβ(x-≧41) in the CSF.

Accordingly, this invention provides methods for screening compounds that elevate or decrease the amount of Aβ(x-≧41) in the CSF and that, therefore, are candidates for use in treating the disease, or that hasten the disease and are to be avoided by humans. The methods involve measuring a first amount of said one or more soluble Aβ(x-≧41) in the CSF of a non-human animal used as a model of Alzheimer's disease; administering the compound to the animal; measuring a second amount of one or more soluble Aβ(x-≧41) in the CSF of the animal; and comparing the first amount with the second amount, the difference indicating whether the compound increases, decreases, or leaves unchanged the amount of soluble Aβ(x-≧41) in the CSF. The dosage level given to the animal and the amount of time that elapses before measuring the second amount will, of course, depend on the model system.

One useful non-human animal model harbors a copy of an expressible transgene sequence which encodes the Swedish mutation of APP (asparagine$^{595}$-leucine$^5$96). The sequence generally is expressed in cells which normally express the naturally-occurring endogenous APP gene (if present). Murine and hamster models are suitable for this use. Such transgenes typically comprise a Swedish mutation APP expression cassette, in which a linked promoter and, preferably, an enhancer drive expression of structural sequences encoding a heterologous APP polypeptide comprising the Swedish mutation.

The transgenic animals that harbor the transgene encoding a Swedish mutation APP polypeptide are usually produced by introducing the transgene or targeting construct into a fertilized egg or embryonic stem (ES) cell, typically by microinjection, electroporation, lipofection, or biolistics. The transgenic animals express the Swedish mutation APP gene of the transgene (or homologously recombined targeting construct), typically in brain tissue. Preferably, one or both endogenous APP allele is inactivated and incapable of expressing the wild-type APP.

The following examples are offered by way of illustration, not by way of limitation.

EXPERIMENTAL

Materials and Methods

1. Antibody Preparation.

a. Monoclonal Antibodies to the Aβ Junction Region.

Monoclonal antibodies to the junction region of Aβ were prepared using a synthetic peptide spanning amino acid residues 13–28, except that NK, amino acids 27 and 28, were substituted with GC. This peptide was called $A\beta_{13-28}$. $A\beta_{13-28}$ was conjugated to an immunogen (a-CD3E antibody; Clone No. 145-2C11, Boehringer-Mannheim) using m-maleimidobenzoyl-N-hydroxysuccinimide ester (MBS) according to the manufacturer's (Pierce) instructions.

A/J mice were immunized initially intraperitoneally (IP) with the Aβ conjugate mixed with complete Freund's adjuvant. Fourteen days later, the mice were boosted IP with the Aβ conjugate mixed with phosphate buffered saline (PBS) at 14 day intervals. After six total boosts, the mice were finally boosted intravenously with Aβ conjugate mixed with incomplete Freund's adjuvant and fused 3 days later. Fusion of spleen cells with P3.653 myeloma cells was performed according as described in Oi and Herzenberg, *Selective Methods in Cellular Immunology*, Mishell and Shigii, Eds., W.H. Freeman and Company, San Francisco, Chapter 17 (1980). Serum titers and initial screens were performed by the RIA method described below. Several clones were expanded to a 24-well plate and subjected to further analysis as described below. Clones of interest were produced in mouse ascites.

The RIA method used to screen serum bleeds and fusion hybridoma supernatants was based upon a method developed by Wang et al. (1977) J. Immunol. Methods 18:157–164. Briefly, the supernatant (or serum) was incubated overnight at room temperature on a rotator with $^{125}$I-labeled $A\beta_{1-28}$ and Sepharose® 4B beads to which sheep anti-mouse IgG had been coupled via cyanogen bromide. The beads from each well were harvested onto glass fiber filter discs with a cell harvester and washed several times with PBS. The filter discs were then transferred to gamma tubes and the bound radioactivity was counted in a gamma counter.

All hybridomas were tested for binding to $A\beta_{1-28}$ using the method described above in the initial screen, and then retested 3 days later. $A\beta_{1-28}$ positive clones were further characterized for reactivity to $^{125}$I-labeled $A\beta_{1-16}$ using the RIA method described above. No clones were found to bind $A\beta_{1-16}$. In a peptide capture ELISA, all clones were found to react with $A\beta_{13-28}$ while no clones reacted to $A\beta_{17-28}$. Therefore, it was determined that all clones had an epitope within the junction region spanning amino acids 16 and 17.

Based on results of the above assays, several clones were expanded into 24 well plates. These clones were further characterized by saturation analysis. Supernatants at the 50% titer point (as determined by the RIA method described above) were added to wells containing Sepharose®-sheep anti-mouse IgG beads, a constant amount of $^{125}$I-labeled $A\beta_{1-28}$ and varying amounts of unlabeled $A\beta_{13-28}$ or $A\beta_{17-28}$. The concentration of cold peptide for 50% inhibition was determined for each antibody. For the $A\beta_{17-28}$, no inhibition was seen at 100 ng/well for any clones. The 50% inhibition point for $A\beta_{13-28}$ ranged from 10–80 ng/well. The clones were also characterized based on reactivity in Western blots. Based on titer point, sensitivity (as determined by the 50% inhibition point), and reactivity on Western blot, several clones were produced in ascites. Antibodies from hybridoma designated 266 was selected for use as a capture antibody in the assays described below.

b. Polyclonal Antibodies to the C-terminal Epitope Containing Amino Acids 33–42 of Aβ

Polyclonal antibodies were generated against Aβ(33–42) as follows. Peptide 277-2 (C-aminoheptanoic-GLIVGGVVIA [SEQ ID NO:2]) was conjugated to cationized BSA (Pierce activated "Supercarrier") at a ratio of 5 mg of 277-2 peptide to 10 mg of cationized BSA as follows. One vial of Pierce Supercarrier (10 mg) was resuspended in 1 mL of deionized water. 5 mg of the 277-2 peptide was dissolved in 5 ml of 10 MM $PO_4$ pH 8.0. The 277-2 peptide was added to the Supercarrier and incubated overnight at room temperature. This was then concentrated and the EDTA removed.

The immunogen (500 mg of peptide equivalent) was injected subcutaneously in complete Freund's adjuvant. Rabbits received a booster of 0.2–0.5 mg after three weeks and 0.2 to 0.5 mg at two to four week intervals thereafter. Boosters were subcutaneously administered in incomplete Freund's adjuvant 25 ml of serum was collected one week after each boost. Bleeds were screened as follows. Week 7 of the rabbit bleeds were titered by serial dilution. ELISA plates were coated with Aβ 1–42 overnight, and then blocked with 3% gelatin. Serial dilutions of the rabbit bleeds from 1/100–1/200,000 were incubated on the plates for 2 hours at room temperature. The plates were then washed and the anti rabbit HRP was added to each well. This incubated for one hour. The plate was washed and TMB substrate was used. ELISA titer of the rabbits was 1/20,000–1/200,000.

The ELISA positive rabbit bleeds were then titered in a capture RIA to compare its ability to capture $^{125}$I Aβ(1–42) versus $^{125}$I Aβ(1–40). Dilutions of rabbit antiserum from 1/25–1/675 were incubated with approximately the same number of cpm's of both tracers. Protein A sepharose was used to precipitate the immune complexes and they were then counted on a Microbeta scintillation counter. 277-2 rabbit D showed the highest titer to Aβ(1–42) tracer and no cross reaction with Aβ(1–40) tracer. The highest titer bleeds were then subjected to affinity purification of antibodies.

To affinity purity anti-277-2 antibodies, a 277-2 affinity matrix was prepared as follows: three ml of sulfo-link gel (Pierce) was washed with six volumes of 50 mM Tris, 5 mM EDTA, pH 8.5. Three mg of 277-2 peptide dissolved in 0.3 ml DMSO was brought to 3 ml with 50 mM Tris, 5 mM EDTA pH 8.5. and added to the gel. After gentle mixing for 15 minutes, the column resin was washed with six volumes of 50 mM Tris, 5 mM EDTA, 0.5 M NaCl pH 8. The column resin was then washed with 16 volumes of PBS/0.05% $NaN_3$.

To affinity purify the antibodies, 20 ml of high titer serum was diluted to 40 ml with PBS and an equal volume of saturated $(NH_4)_2SO_4$ was slowly added while stirring at 40. The mixture was allowed to stir an additional 30 minutes then spun for 15 minutes at 10,000 rpm in a Beckman JA17 rotor. The pellets were resuspended in PBS, brought to a volume of 40 ml with PBS and the $(NH_4)_2SO_4$ precipitation repeated as above.

The pellets were resuspended in a total of 20 ml of PBS and dialyzed overnight against PBS at 4°.

The 277-2 column was washed with 10 ml of PBS. Then the dialyzate was run over the column. The column was then washed with 50 ml of PBS. 0.1 M glycine, 0.5 M NaCl pH 2.5 was added 1 ml at a time and fractions collected. The first four fractions containing the majority of elated protein were pooled and neutralized with 0.4 ml of 1 M Tris pH 8.0. The pool was concentrated by membrane filtration to slightly less than 2 ml. The initial column flow-through was subjected to a second chromatographic step (after first neutralizing the column and reequilibrating it in PBS). The second affinity-purified material was similarly neutralized and concentrated, combined with the first material and then dialyzed against PBS overnight, 4°. The protein content was determined (Pierce BCA method) and these antibodies were used in ELISA experiments.

2. ELISA Assay.

a. Binding of Capture Antibody to Microtiter Wells.

Monoclonal antibody 266 was diluted to a concentration of 10 μg/ml in a buffer containing 0.23 g/L $NaH_2PO_4 \cdot H_2O$, 26.2 g/L $Na_2HPO_4$; $7H_2O$, 1 g/L $NaN_3$, pH 8.5. One hundred μl/well of this solution was then dispensed in a 96 well white Dynatech Microlite 2, 96 well flat-bottomed plate. The plates were sealed and incubated overnight at room temperature. Following coating, the remaining solution was aspirated and the non-specific binding sites were blocked with 200 μL per well of ($NaH_2PO_4 \cdot H_2O$) 0.2 g/L, $Na_2HPO_4 \cdot 7H_2O$ 0.8 g/L, human serum albumin (HSA) crystallized and lyophilized 2.5 g/L, pH 7.4. These plates were blocked by incubating for 1 hour at room temperature in the blocking solution.

c. Monoclonal Antibodies to the N-terminal Region of βAP.

Monoclonal antibodies to the N-terminal region of βAP were prepared using a synthetic peptide spanning amino acid residues 1–28 ($βAP_{1-28}$). $βAP_{1-28}$ was chemically coupled using disuccimidyl suberate (DSS) to rabbit serum albumin (RSA) using a 20:1 molar ratio of peptide to protein in 50 mM sodium phosphate, pH 7.0, 150 mM NaCl, overnight at 21° C. using 1 mM DSS (Hyman et al. (1992) J. Neuropath. Exp. Neuro. 51:76).

Antibodies 10D5 and 6C6 were obtained from a fusion where mice had received 5 injections of $βAP_{1-28}$ coupled to RSA via DSS at 100 μg/ml. The initial injection was in complete Freund's adjuvant (CFA) followed by second and subsequent injections in incomplete Fruend's adjuvant (IFA) every 10–14 days. Three days before the fusion, mouse 4 which had a titer of 1/70,000 as measured by ELISA against $βAP_{1-28}$, received 100 μg of $βAP_{1-28}$ RSA in PBS intraperitoneally as a final boost. Screening was done by ELISA and on paraffin-fixed AD brain sections. The coating concentration of $βAP_{1-28}$ was 1 μg/well. 10D5 and 6C6 were positive by ELISA and AD brain tissue section.

b. Assay Protocol.

The calibrators were prepared from a stock solution of $Aβ_{1-42}$, 1 g/ml, in DMSO. In specimen diluent (($NaH_2PO_4 \cdot H_2O$) 0.2 g/L, $Na_2HPO_4 \cdot 7H_2O$ 2.16 g/L, $NaN_3$ 0.5 g/L, bovine serum albumin (BSA) (globulin free) 6 g/L, triton x-405 0.5 ml/L NaCl 8.5 g/L, pH 7.4.), the highest calibrator, 1000 pg/ml (10 μl $Aβ_{1-42}$ stock (1 μg/ml DMSO) in 10 ml casein specimen diluent) was prepared. Sequential dilutions were made in specimen diluent to obtain 500, 250, 125, 62.5 and 31.25 pg/ml concentrations of $Aβ_{1-42}$.

CSF samples were prepared as follows. The CSF samples (100–500 μl) were boiled for 3 minutes. The boiled samples were placed at 4° C. for 10–14 hours before assaying. CSF samples are assayed undiluted. Dilutions are only made if the initial calculated value is above the highest calibrator (1000 pg/ml).

One hundred μL per well calibrators or samples were applied to the microtiter plates. The plates were sealed and incubated for 1 hour at room temperature. The plates were then washed three times with washing buffer (NaCl 80 g/L, KCl 3.85 g/L, Tris-HCl 31.75 g/L, tween-20 0.5 ml/L, pH 7.5).

Anti-Aβ(33–42) (antibody 277-2) was diluted in specimen diluent to 1 μg/ml and 100 μl was added per well. The plate was covered and incubated for 1 hour at room temperature. The plate was washed three times with washing buffer. The alkaline phosphatase affinity purified F(ab')2 fragment donkey anti-rabbit IgG (H+L) (Jackson) was diluted 1:1000 in specimen diluent. One hundred μl/well was added. The plate was covered and incubated for 1 hour at room temperature. The plate was washed three times with washing buffer, then 100 μl/well of chemiluminescent substrate was added. The chemiluminescent substrate was prepared by diluting the chemiluminescent reagent, AMPPD (Tropix), and an enhancer, emerald green (Tropix), 1:1000 and 1:100 respectively in 1M diethanolemine buffer, pH 10, containing 1 mM $MgCl_2$ and 0.2% $NaN_3$. The plates were sealed and incubated for 10 to 15 minutes at room temperature. Solution was not aspirated. This time may have to be optimized for different antibody lots.

Chemiluminescence was read and expressed as relative chemiluminescence units (CLU) after 15 minutes using a Dynatech ML 1000.

Results

1. Aβ(x-≧41) Assay Specificity

Aβ(x-≧41) ELISA does not cross-react with Aβ(1–28), (1–38), or (1–40) (FIG. 1).

2. Aβ(x-≧41) Assay Sensitivity

The lower sensitivity limit for this assay is 31 pg/ml or 3.1 pg/well (0.7 fmol/well) (FIG. 1).

3. Aβ(x-≧41) Levels in CSF

Aβ(x-≧41) has been verified in CSF using the Aβ(x-≧41) ELISA. On occasion, two different groups of CSF samples, designated Group A and Group B, were obtained from various sources. Sometimes, two hundred μl of the CSF samples were boiled for 3 minutes prior to assay (boiling was found to increase Aβ(x-≧41) immunoreactivity in some cases). The results of this assay can be seen in FIG. 2 and FIG. 3. Table 1 summarizes these results.

TABLE I

AD DIAGNOSTICS
Aβ(x-≧41) Data
Groups A and B CSF

| GROUP | Aβ1–42(pg/mL) CUTOFF | SENSITIVITY FOR AD* | SPECIFICITY FOR AD |
|---|---|---|---|
| Group A | ≦362.7 | 50% | 84% |
|  | ≦588.0 | 93.8% | 50.0% |
| Group B | ≦367.4 | 50% | 85% |
|  | ≦504.4 | 97.4% | 56.6% |

*Equal to specificity for detecting that an individual does not have AD.

4. Aβ(x-≧41) in CSF of Rodents and Dogs

Aβ(x-≧41) immunoreactivity was also detected in CSF of guinea pigs, rats and dogs (Table II).

TABLE II

Aβ IMMUNOREACTIVITY
IN THE CSF OF VARIOUS ANIMAL SPECIES

| SPECIES | TOTAL Aβ(ng/ml) | Aβ(X-≧41) (ng/ml) | % Aβ(x-≧41) |
|---|---|---|---|
| Rat | 1.7 | 0.235 | 13.8 |
| Guinea Pig | 4.5 | 0.242 | 5.4 |
| Dog | 4.4 | 0.59 | 13.4 |

This sandwich ELISA demonstrates the presence of Aβ(x-≧41) in CSF. Aβ(x-≧41) is only a minor component of the total Aβ in CSF. The levels of Aβ(x-≧41) in CSF are significantly lower in AD than normal and neurological controls. Taking a 50% sensitivity limit, the specificity is 93.8 for Group A and 97.4% for Group B. These two independent groups show a remarkable similarity demonstrating that measurements of Aβ(x-≧41) in CSF have diagnostic utility.

Although the foregoing invention has been described in detail for purposes of clarity of understanding, it will be obvious that certain modifications may be practiced within the scope of the appended claims.

What is claimed is:

1. A method for diagnosing probable Alzheimer's disease in a patient, the method comprising:

measuring the amount of one or more soluble amyloid-β peptide(x-$\geq$41) ("Aβ(x-$\geq$41)") in a cerebrospinal fluid sample of the patient;

comparing the measured amount with a predetermined indicator value of the one or more soluble Aβ(x-$\geq$41); and assessing patient status based on a difference between the measured amount and the predetermined indicator value, wherein a measured amount above the indicator value provides a negative indication in the diagnosis of probable Alzheimer's disease and a measured amount at or below the indicator value provides a positive indication in the diagnosis of probable Alzheimer's disease.

2. The method of claim 1 wherein the amount of the soluble Aβ(x-$\geq$41) is measured by:

capturing the soluble Aβ(x-$\geq$41) from the sample on a solid phase with a first antibody or antibody fragment specific for an epitope within a junction region of Aβ disposed between amino acids 13–26; and detecting capture of the soluble Aβ(x-$\geq$41) using a second antibody or antibody fragment specific for Aβ(x-$\geq$41).

3. The method of claim 2 wherein the detecting step comprises detecting binding between the second antibody or antibody fragment and Aβ(3(x-$\geq$41) using a third labelled antibody or antibody fragment that recognizes the second antibody or antibody fragment but not the first antibody or antibody fragment.

4. The method of claim 3 wherein the label is an enzymatic label.

5. The method of claim 2 wherein the first antibody or antibody fragment has the specificity of an antibody raised against Aβ$_{13-28}$.

6. The method of claim 2 wherein the second antibody or antibody fragment has the specificity of an antibody raised against amino acids 33–42 of Aβ.

7. The method of claim 6 wherein the first antibody or antibody fragment has the specificity of an antibody raised against Aβ$_{13-28}$.

8. The method of claim 1 wherein the amount of the soluble Aβ(x-$\geq$41) is measured by:

capturing the soluble Aβ(x-$\geq$41) from the sample on a solid phase with a first antibody or antibody fragment specific for Aβ(x-$\geq$41); and detecting capture of the soluble Aβ(x-$\geq$41) using a second antibody or antibody fragment that recognizes Aβ.

9. The method of claim 8 wherein the detecting step comprises detecting binding between the second antibody or antibody fragment and Aβ(x-$\geq$41) using a third labelled antibody or antibody fragment that recognizes the second antibody or antibody fragment but not the first antibody or antibody fragment.

10. The method of claim 9 wherein the label is an enzymatic label.

11. The method of claim 8 wherein the first antibody or antibody fragment has the specificity of an antibody raised against amino acids 33–42 of Aβ.

12. The method of claim 11 wherein the second antibody or antibody fragment recognizes an N-terminal region of Aβ.

13. The method of claim 8 wherein the second antibody or antibody fragment is specific for an epitope within a junction region of Aβ disposed between amino acids 13–26.

14. The method of claim 13 wherein the second antibody or antibody fragment has the specificity of an antibody raised against Aβ$_{13-28}$.

15. The method of claim 1 wherein the amount of the soluble Aβ(x-≧41) is measured by:

capturing the soluble Aβ(x-≧41) from the sample on a solid phase with a first antibody or antibody fragment specific for Aβ; and detecting capture of the soluble Aβ(x-≧41) using a second antibody or antibody fragment specific for Aβ(x-≧41).

16. The method of claim 15 wherein the detecting step comprises detecting binding between the second antibody or antibody fragment and Aβ(x-≧41) using a third labelled antibody or antibody fragment that recognizes the second antibody or antibody fragment but not the first antibody or antibody fragment.

17. The method of claim 16 wherein the label is an enzymatic label.

18. The method of claim 15 wherein the second antibody or antibody fragment has the specificity of an antibody raised against amino acids 33–42 of Aβ.

19. The method of claim 18 wherein the first antibody or antibody fragment recognizes an N-terminal region of Aβ.

20. The method of claim 1 wherein Aβ(x-≧41) is Aβ(x-42).

* * * * *

UNITED STATES PATENT AND TRADEMARK OFFICE
CERTIFICATE OF CORRECTION

PATENT NO. : 6,114,133
DATED : September 5, 2000
INVENTOR(S) : Peter A. Seubert, et al.

It is certified that error appears in the above-identified patent and that said Letters Patent is hereby corrected as shown below:

Column 16, line 43, replace "$A\beta(3(x-\geq41)$" with -- $A\beta(x-\geq41)$ --.

Signed and Sealed this

Seventeenth Day of April, 2001

Attest:

NICHOLAS P. GODICI

*Attesting Officer*  *Acting Director of the United States Patent and Trademark Office*

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 43 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Asp Ala Glu Phe Arg His Asp Ser Gly Tyr Glu Val His His Gln Lys
1               5                   10                  15

Leu Val Phe Phe Ala Gly Asp Val Gly Ser Asn Lys Gly Ala Ile Ile
            20                  25                  30

Gly Leu Met Val Gly Gly Val Val Ile Ala Thr
        35                  40
```

(2) INFORMATION FOR SEQ ID NO:2:

(i) SEQUENCE CHARACTERISTICS:
      (A) LENGTH: 10 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:2:

```
Gly Leu Met Val Gly Gly Val Val Ile Ala
1               5                   10
```